(12) United States Patent
Guo et al.

(10) Patent No.: US 10,076,639 B2
(45) Date of Patent: Sep. 18, 2018

(54) BODY FOR A CATHETER OR SHEATH

(71) Applicant: St. Jude Medical, Atrial Fibrillation Division, Inc., St. Paul, MN (US)

(72) Inventors: Xiaoping Guo, Eden Prairie, MN (US); Richard E. Stehr, Tuscon, AZ (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 228 days.

(21) Appl. No.: 14/818,633

(22) Filed: Aug. 5, 2015

(65) Prior Publication Data

US 2016/0008583 A1 Jan. 14, 2016

Related U.S. Application Data

(62) Division of application No. 11/910,680, filed as application No. PCT/US2006/016373 on Apr. 28, 2006, now Pat. No. 9,126,019.

(Continued)

(51) Int. Cl.
*A61M 5/178* (2006.01)
*A61M 31/00* (2006.01)
(Continued)

(52) U.S. Cl.
CPC ...... *A61M 25/0668* (2013.01); *A61M 25/005* (2013.01); *A61M 25/0009* (2013.01); *A61M 25/0023* (2013.01); *A61M 25/0108* (2013.01)

(58) Field of Classification Search
CPC .......... A61M 25/0668; A61M 25/0009; A61M 25/0023; A61M 25/005; A61M 25/0108; A61M 2025/0687; A61M 25/001
See application file for complete search history.

(56) References Cited

U.S. PATENT DOCUMENTS 4,402,685 A  9/1983 Bühler et al.
4,469,483 A  9/1984 Becker et al.
(Continued)

FOREIGN PATENT DOCUMENTS

DE  3635695  9/1987
EP  0010757  5/1980
(Continued)

OTHER PUBLICATIONS

International Search Report and Written Opinion for PCT/US06/16373 dated Jan. 26, 2007.

*Primary Examiner* — Rebecca E Eisenberg
(74) *Attorney, Agent, or Firm* — Wiley Rein LLP

(57) ABSTRACT

A body (2) for a catheter or sheath is disclosed. The body (2) includes strips (8, 10) formed longitudinally from the proximal (6) portion of the body (2) to the distal (4) portion of the body (2). The strips are formed of different materials. The strips can have different radiopacities, or can be splittable/peelable. The splittable/peelable body comprises a peel mechanism longitudinally extending along its respective length. The peel mechanism can be formed by longitudinally extending regions of interfacial bonding between first and second longitudinally extending strips of polymer material. A region of stress concentration extends along the region of interfacial bonding. The stress concentration facilitates the splitting of the body (2) along its peel mechanism. The polymer material of the first strip (8) can have a greater amount of radiopaque filler than the polymer material of the second strip (10). Each strip forms at least a portion of an outer circumferential surface of the body (2).

19 Claims, 7 Drawing Sheets

Related U.S. Application Data

(60) Provisional application No. 60/675,973, filed on Apr. 28, 2005.

(51) Int. Cl.
*A61M 37/00* (2006.01)
*A61M 25/06* (2006.01)
*A61M 25/00* (2006.01)
*A61M 25/01* (2006.01)

(56) References Cited

U.S. PATENT DOCUMENTS

| | | | |
|---|---|---|---|
| RE31,855 E * | 3/1985 | Osborne | A61M 25/0668 604/161 |
| 4,772,266 A * | 9/1988 | Groshong | A61M 25/0668 604/160 |
| 4,781,690 A | 11/1988 | Ishida et al. | |
| 4,983,168 A | 1/1991 | Moorehead | |
| 5,320,602 A | 6/1994 | Karpiel | |
| 5,947,953 A | 9/1999 | Ash et al. | |
| 6,146,814 A | 11/2000 | Millet | |
| 6,190,349 B1 | 2/2001 | Ash et al. | |
| 6,200,338 B1 | 3/2001 | Solomon et al. | |
| 2004/0267203 A1 | 12/2004 | Potter et al. | |
| 2005/0075626 A1 | 4/2005 | Venturelli | |

FOREIGN PATENT DOCUMENTS

| | | |
|---|---|---|
| EP | 0021446 | 1/1981 |
| EP | 0238018 | 9/1987 |
| EP | 0245837 | 11/1987 |
| EP | 0279015 | 8/1988 |
| EP | 0472413 | 2/1992 |
| JP | 11188799 | 7/1999 |
| JP | 2000014764 | 1/2000 |
| JP | 2004321223 | 11/2004 |
| WO | 99/48548 | 9/1999 |
| WO | 2003/039639 | 5/2003 |

* cited by examiner

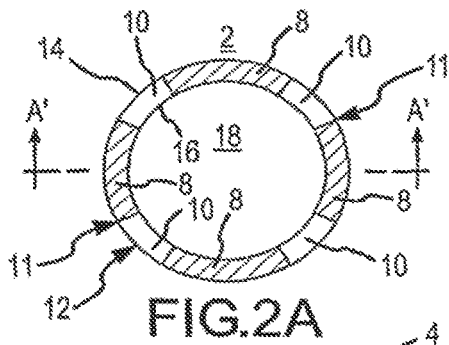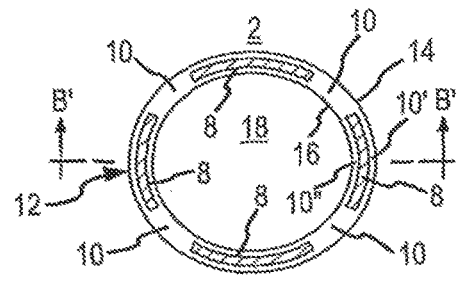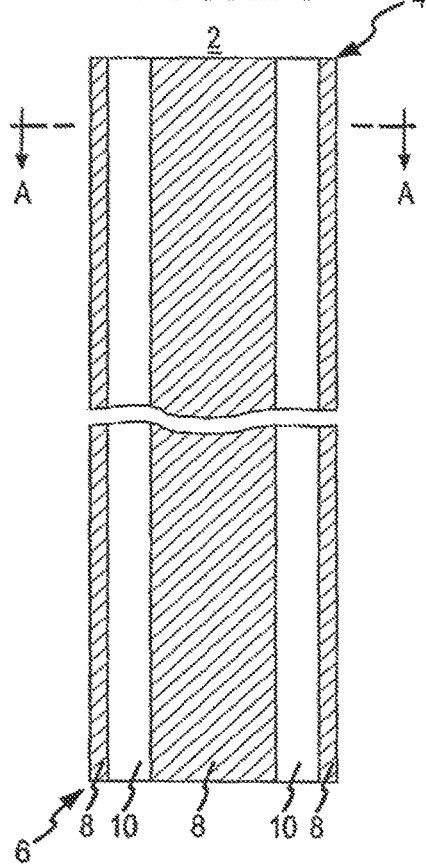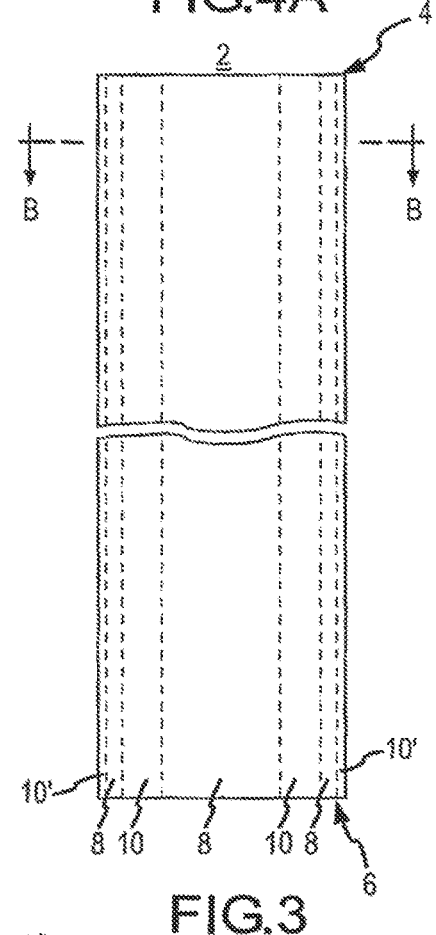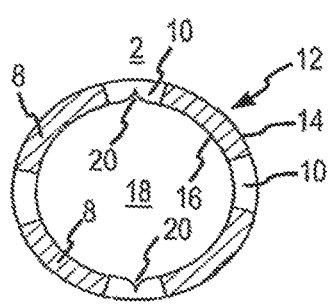

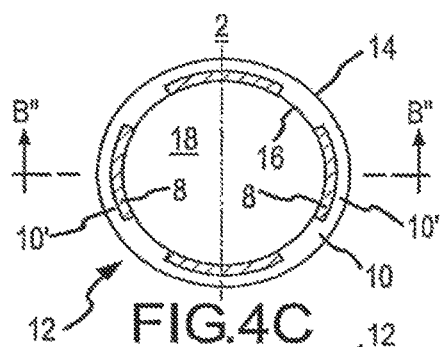
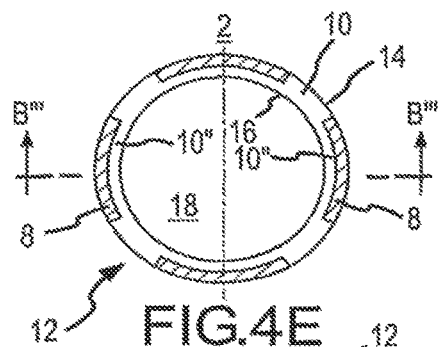
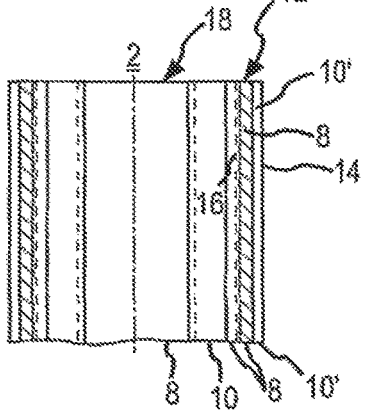
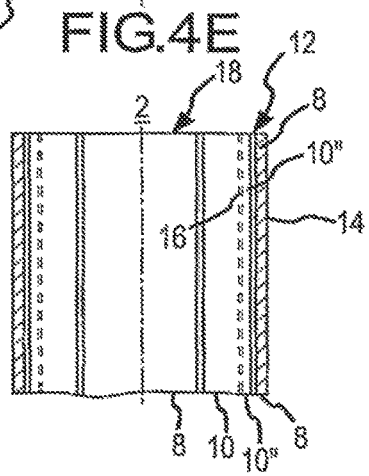
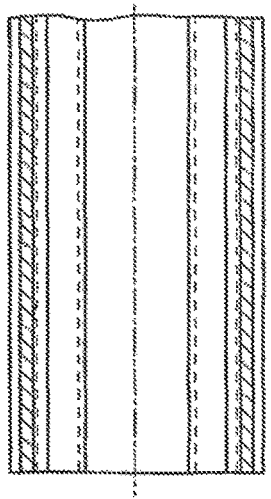
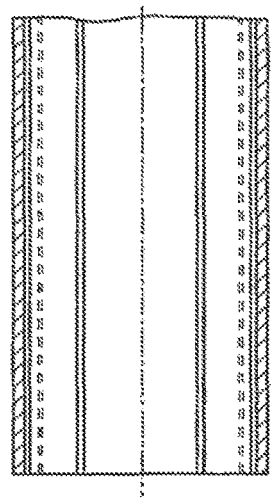
FIG.4D  FIG.4F

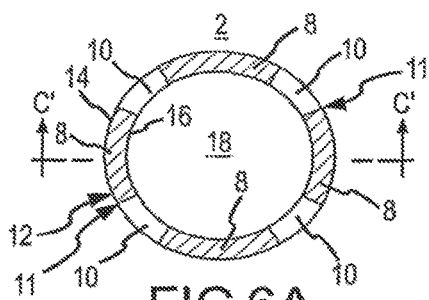
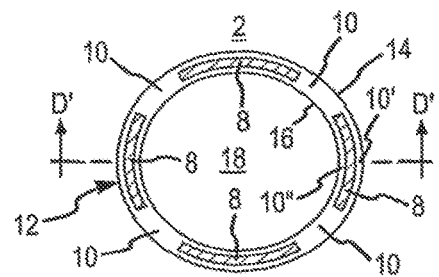
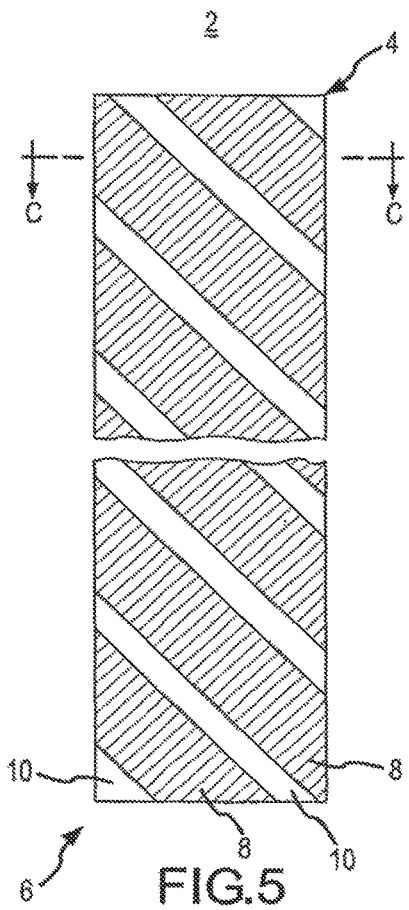
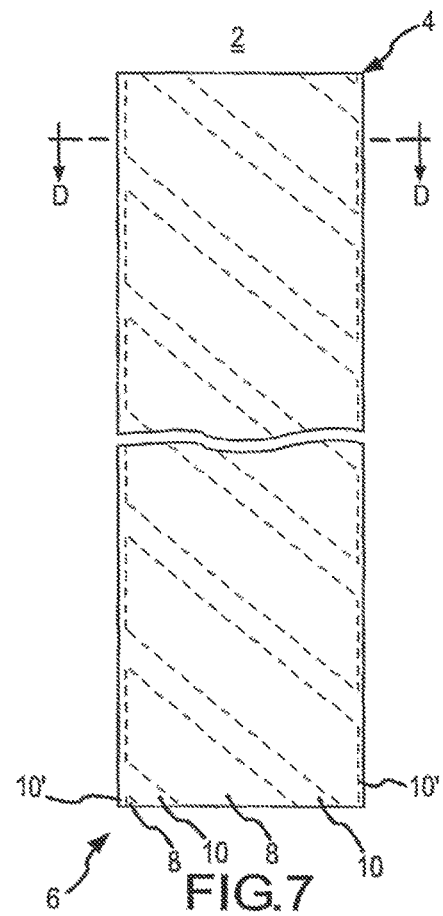

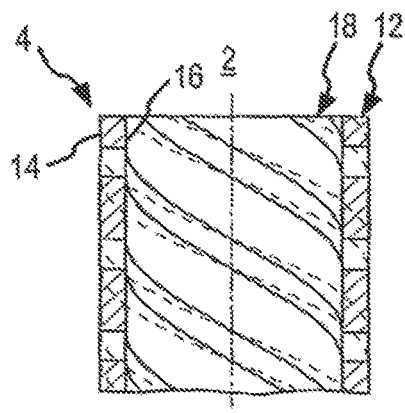
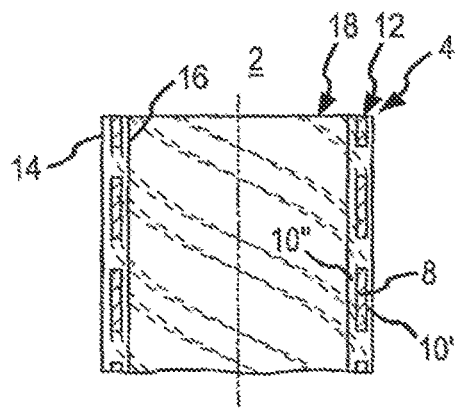
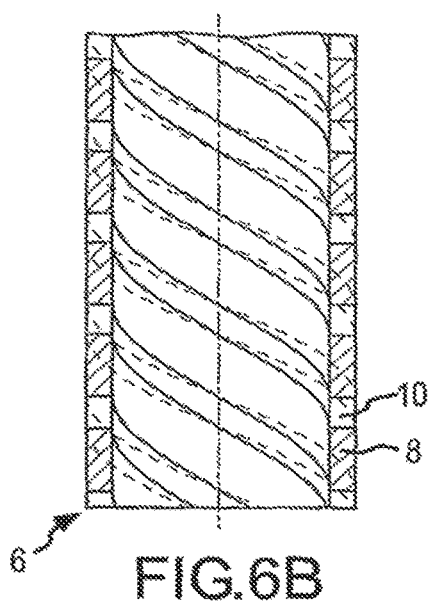
FIG.6B
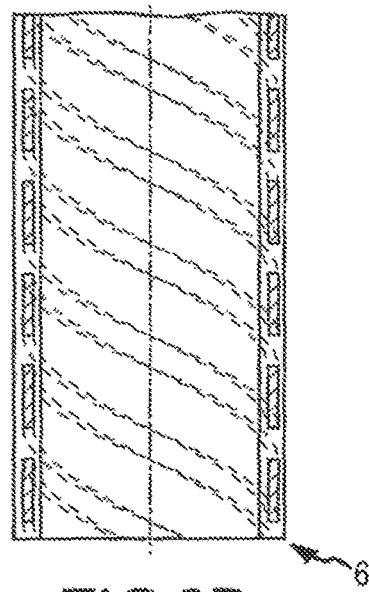
FIG.8B

BODY FOR A CATHETER OR SHEATH

CROSS-REFERENCE TO RELATED APPLICATIONS

This application is a divisional U.S. application Ser. No. 11/910,680, filed 4 Oct. 2007 (the '680 application), now U.S. Pat. No. 9,126,019 which is a national stage application of international application no. PCT/US2006/016373, filed 28 Apr. 2006 (the '373 application), now expired, which in turn claims the benefit of U.S. application No. 60/675,973, filed 28 Apr. 2005 (the '973 application). The '680 application, '373 application, and '973 application are each hereby incorporated by reference as though fully set forth herein.

BACKGROUND OF THE INVENTION

The present invention relates to bodies for catheters and sheaths and methods of manufacturing and using such bodies. More particularly, the present invention relates to splittable and radiopaque bodies and methods of manufacturing and using such bodies.

Catheters and sheaths are commonly manufactured with splittable (i.e., peelable or peel-away) type bodies that allow the catheter or sheath to be removed from about an implanted medical device (e.g., pacemaker leads) without disturbing the device. Prior art bodies are formed with peeling grooves that extend longitudinally along the inner or outer circumferential surfaces of their walls in order to make the bodies splittable. Providing such peeling grooves is a difficult and expensive manufacturing process.

Other catheters and sheaths are commonly manufactured with tubular bodies having radiopaque distal tips. Such catheters and sheaths are used in cardiovascular procedures and other medical procedures. The radiopaque distal tip may be viewed within a patient's body via an X-ray fluoroscope or other imaging system, thereby allowing a physician to position the tubular body as required during a procedure.

Prior art tubular bodies with radiopaque distal tips often use precious heavy metals (e.g., gold, platinum, tantalum) to achieve sufficient tip radiopacity. For example, a thin band of a precious heavy metal is imbedded in the distal tip of each such prior art tubular body. As a result, such prior art tubular bodies end up being quite expensive because of the high cost of the precious heavy metals and the labor intensive manufacturing processes used to manufacture such tubular bodies.

Tubular bodies are made from polymeric materials that may not be chemically compatible with the precious metal used to form the radiopaque distal band. As such, the distal band may not adhere to the material matrix of the tubular body, causing potential material separation and a discontinuity in mechanical strength.

Where a tubular body with a radiopaque distal tip also needs to be splittable to allow its removal from a patient without disturbing an implanted medical device, the thin band of precious heavy metal must be provided with a peeling groove that coincides with the peeling groove in the tubular body's wall. This adds further difficulty and expense to an already difficult and expensive manufacturing process.

There is a need in the art for a splittable and/or radiopaque tubular body that utilizes less costly materials, is less labor intensive to manufacture, and is less likely to fail during a medical procedure due to material separation. There is also a need for methods of manufacturing and using such a tubular body.

BRIEF SUMMARY OF THE INVENTION

The present invention is a body for a catheter or sheath. The body comprises a lumen defined by a wall formed with longitudinal strips. The first strip has a radiopacity that is higher than the second strip, providing the body with required visibility within a patient's body via an x-ray fluoroscope. The body can have a tubular cross section as described in detail herein, or may have any other desirable cross section, e.g., generally triangular or square.

The present invention is a body for a catheter or sheath. The body includes a proximal end, a distal end, a first longitudinal strip, and a second longitudinal strip. The first and second strips extend between the proximal and distal ends. The first strip can have a radiopacity that is higher than the second strip. The first strip can be made of radiopaque polymeric compounds, including tungsten-filled polymer compounds. The first and second strips may be helical along the body.

The first longitudinal strip may comprise between 2-50% of the circumference of the body. The first longitudinal strip may comprise between 10-25% of the circumference of the body. The first longitudinal strip may comprise between 1-5% of the circumference of the body.

The tubular body can include a proximal end, a distal end, a first longitudinal strip, and a second longitudinal strip. The first and second longitudinal strips can be formed at the distal end of the tubular body only, and then bonded together to form the tubular body using various polymeric joining technologies.

The tubular body can have a cylindrical wall. A wall cross-section of the cylindrical wall (as taken generally perpendicular to a longitudinal axis of the cylindrical wall) includes a first wall segment and a second wall segment. These two segments may form at least an integral portion of the wall cross-section, which may be circumferentially continuous and integral. The first segment can have a radiopacity that is higher than the second segment.

The present invention, includes a method of forming a tubular body for a catheter or sheath. The tubular body includes a first longitudinal strip and a second longitudinal strip. The method comprises providing a machine and relevant specialty tool, displacing a first material with the machine to create a first material stream, displacing a second material with the machine to create a second material stream, and bringing the first material stream into contact with the second material stream such that the first material stream forms the first longitudinal strip and the second material stream forms the second longitudinal strip. The first and second strips may form at least a portion of a wall cross-section of the tubular body, wherein the wall cross-section is circumferentially continuous and integral. The first material can have a radiopacity that exceeds the radiopacity of the second material.

The machine can be, for example, a co-extrusion machine, a co-injection molding machine, or a co-compression molding machine.

The tubular body can comprise a peel line formed by a longitudinally extending region of interfacial bonding between first and second longitudinally extending strips of polymer material.

The polymer materials of the first and second strips can differ in that the polymer material of the first strip is loaded with a greater amount of inorganic filler than the polymer material of the second strip. The polymer material of the first strip can have a greater amount of radiopaque material than the polymer material of the second strip. The radiopaque material can include a pure metal or metallic compound with at least one element with an atomic number from about 22 to about 83.

The polymer material of the first longitudinally extending strip can be functionally miscible with the polymer material of the second longitudinally extending strip. The polymer material of the first longitudinally extending strip may be comprised of at least one different polymer than the polymer material of the second longitudinally extending strip.

Each strip can form at least a portion of an outer circumferential surface of the tubular body. A region of stress concentration extends along the region of interfacial bonding. The stress concentration facilitates the splitting of the splittable tubular body along the peel line.

The polymer material of the first strip can be dissimilar from, but chemically compatible with, the polymer material of the second strip. The polymer material of the first strip may have a molecular orientation that is different from a molecular orientation of the polymer of the second strip. For example, the polymer material of the first strip can have a flow-induced axial molecular orientation.

The polymer material of the first strip can be chemically in-compatible with the polymer material of the second strip. If so, a polymer compatibilizer is introduced into at least one of the polymer materials to improve melt adhesion between the first and second strips of polymer material.

The splittable tubular body can include a first peel mechanism longitudinally extending along the body. The first peel mechanism is formed by a longitudinally extending region of interfacial bonding between first and second longitudinally extending strips of polymer material.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is an elevational view of the present invention, according to a first embodiment, including a splittable/peelable body for a catheter or sheath, wherein the body includes a distal end and a proximal end and is formed of at least two integral longitudinal strips of different material.

FIG. 2A is a latitudinal cross-sectional view of the first embodiment of the body taken through section line A-A in FIG. 1.

FIG. 3 is an elevational view of the present invention according to a second embodiment including a splittable tubular body for a catheter or sheath, wherein the tubular body includes a distal end and a proximal end and is formed of at least two integral longitudinal strips of different material.

FIG. 4A is a latitudinal cross-sectional view of the second embodiment of the tubular body taken through section line B-B in FIG. 3.

FIG. 4C is a latitudinal cross-sectional view of a first variation of the second embodiment of the tubular body taken through section line B-B in FIG. 3.

FIG. 4D is a longitudinal cross-sectional view of the first variation of the second embodiment of the tubular body taken through section line B"-B" in FIG. 4C.

FIG. 4E is a latitudinal cross-sectional view of a second variation of the second embodiment of the tubular body taken through section line B-B in FIG. 3.

FIG. 4F is a longitudinal cross-sectional view of the second variation of the second embodiment of the tubular body taken through section line B"-B'" in FIG. 4E.

FIG. 5 is an elevational view of the present invention according to a third embodiment including a splittable tubular body for a catheter or sheath, wherein the tubular body includes a distal end and a proximal end and is formed of at least two integral longitudinal helical strips of different material.

FIG. 6A is a latitudinal cross-sectional view of the third embodiment of the tubular body taken through section line C-C in FIG. 5.

FIG. 6B is a longitudinal cross-sectional view of the third embodiment of the tubular body taken through section line C'-C' in FIG. 6A.

FIG. 7 is an elevational view of the present invention according to a fourth embodiment including a splittable tubular body for a catheter or sheath, wherein the tubular body includes a distal end and a proximal end and is formed of at least two integral longitudinal helical strips of different material.

FIG. 8A is a cross-sectional view of the fourth embodiment of the tubular body taken through section line D-D in FIG. 7.

FIG. 8B is a longitudinal cross-sectional view of the fourth embodiment of the tubular body taken through section line D'-D' in FIG. 8A.

FIG. 9 is similar to FIG. 2A, but is a cross-sectional view of the present invention according to a fifth embodiment, including a splittable tubular body, wherein the tubular body has integral peel grooves that can be located in either the first or the second longitudinal strips.

DETAILED DESCRIPTION OF THE INVENTION

Figure 10:
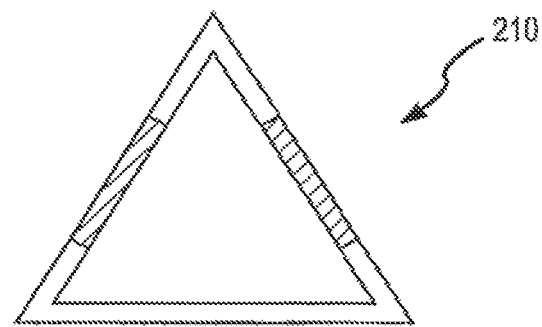
FIG. 10 is a cross-sectional view of a sixth embodiment of the splittable body, including a triangular cross-section.
Figure 11:
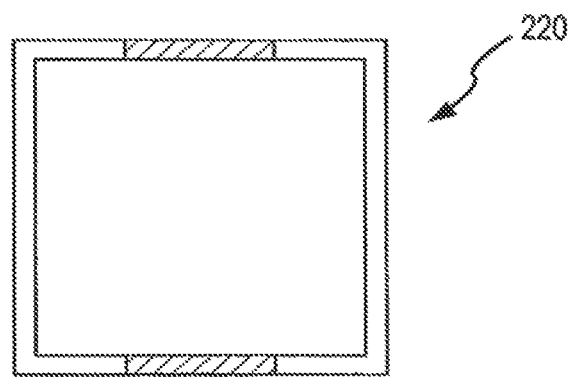
FIG. 11 is a cross-section view of a seventh embodiment of the splittable body, including a square cross-section.

FIG. 1 is an elevational view of the present invention according to a first embodiment including a splittable (i.e., peel-away type) body 2 for a catheter or sheath. The body 2 includes a distal end 4 and a proximal end 6. As shown in FIG. 1, the body 2 is formed of at least two integral longitudinal strips 8, 10 of different materials. As indicated in FIG. 1, each strip 8, 10 may extend the full length of the tubular body 2 in a generally straight manner. As shown in FIG. 2a, the body can have a tubular cross section. As shown in FIGS. 10 and 11, the body can have a triangular 210 or square 220 cross-section.

The strips 8, 10 will be referred to herein as the first strip 8 and the second strip 10. The material of the first strip 8 will be sufficiently different from the material of the second strip 10 so as to form a stress concentration along the interfacial zones (i.e., borders) 11 between the two strips 8, 10. The stress concentration forms a peel line 11 that acts like a built-in peel groove. As a result, the tubular body 2 is readily splittable although it lacks an actual peel groove.

The dissimilarity between the materials used to form the strips 8, 10 need only be sufficient enough to create a stress concentration that acts as a built-in peel groove. This may be accomplished in different ways, including the following ways.

The materials used for the strips 8, 10 may be generally the same, but can also differ. For example, the first strip 8 may be constructed from a first polymer and the second strip 10 may be constructed from a second polymer. The polymer used for the first strip 8 may have a different molecular orientation than the polymer used for the second strip 10. In one embodiment, the material used for the first strip 8 is a polymer with flow-induced axial molecular orientation, and the material used for the second strip 10 is a polymer having little or no flow-induced axial molecular orientation. In such an embodiment, the tear strength along the flow-induced orientation direction for the polymeric material used for the first strip 8 will decrease due to the mechanical anisotropy induced by the molecular chain alignment. Conversely, due to its low level of mechanical anisotropy, the polymeric material used for the second strip 10 will have any one or all of the following attributes: high tear strength; high mechanical strength, high torquability; and high kink resistance. Examples of materials that can be used for the first strip 8 and are easily molecularly oriented along the flow direction during polymer processing include, among other materials, crystal polymers like Ticona Vectra™, LKX 1107, and LKX 1113.

The base polymer materials used for the first and second strips 8, 10 can be chemically the same or similar, except, the material used for the first strip 8 can be loaded with semi-compatible or incompatible inorganic fillers. Such fillers can include radiopaque fillers or other general-purpose fillers like silica, clay, graphite, mica, and calcium carbonate. The tear strengths and the elongations at yield and break for the material used for the first strip 8 will decrease with the increase of the filler loading.

The base polymeric materials used for the first and second strips 8, 10 can be chemically in-compatible. If so, a polymer compatibilizer is introduced to at least one of the polymer materials used for the first and second strips 8, 10 to improve the melt adhesion between the first and second strips 8, 10.

After the tubular body 2 is manufactured, the material used for the first strips 8 can be different from the material used for the second strip 10 with respect to molecular orientation and/or anisotropy in mechanical properties. This will especially be the case with respect to tear strength and elongation at yield and break. Furthermore, the materials used for the first and second strips 8, 10 will be at least partially compatible such that self-adhesion interfacial zones 11 are reliably formable between the strips 8, 10.

The materials used for the strips 8, 10 can be functionally miscible. To be functionally miscible, the two materials used for the strips 8, 10, must have sufficient adhesion to function for the intended use of the instrument, but must have sufficient stress concentrations formed at the interfacial zones 11 between the strips 8, 10 to readily act as a built-in peel groove when the instrument has completed its intended function. In another embodiment, the materials used for the strips 8, 10 are chemically miscible or partially miscible in order to impose the self-adhesion of the strips 8, 10 and create reliable interfacial regions 11 between said strips 8, 10. In one embodiment, the materials used for the strips 8, 10 include melt-processable thermoplastics (e.g., polyethylene, polyvinylidene fluoride, fluorinated ethylene-propylene copolymer, Polyethylene-co-tetrafluoroethylene, plypropylene, polyamide-6, polyamide-6.6, polyamide-11, polyamide-12, polyethylene terephathlate, polybutylenes terephathlate, polycarbonates, polystyrene, etc.) and thermoplastic elastomers ("TPEs") (e.g., polyamide-based TPEs, olefinic TPEs, ionic TPEs, polyester-based TPEs, thermoplastic polyurethanes, etc.).

The material used for the first strip 8 can be a material highly loaded with a radiopaque material. In such an embodiment, the first strip 8 is referred to as the high radiopacity strip(s) 8. In the same embodiment, the material used for the second strip 10 is a material that is not loaded or a material that is lightly loaded with a radiopaque material. In such an embodiment, the second strip 10 is referred to as the low radiopacity strip(s) 10.

As will described in greater detail later in this Detailed Description, the tubular body 2 is inserted into the body of a patient via a surgical site (e.g., entering the chest cavity below the xiphoid process) and directed to a point of treatment (e.g., the pericardial space of a heart). Alternatively, the tubular body 2 is inserted into the body of a patient via a body lumen of a patient (e.g., a blood vessel) and manipulated so it travels along the body lumen to a point of treatment (e.g., a chamber in the heart). A medical device is implanted at the point of treatment via the tubular body 2. To allow the removal of the tubular body 2 without disturbing the implanted medical device (e.g., pacemaker leads), the tubular body 2 is longitudinally split along the interfaces 11 between the strips 8, 10 by simply forcing the sides of the tubular body 2 apart via a fingernail, tool or other implement. The stress concentrations 11 formed at the interfaces 11 between the strips 8, 10 act as a built-in peel groove. The split tubular body 2 is then removed from about the implanted medical device.

Where the tubular body 2 includes a first strip 8 formed from a material that is highly-loaded with a radiopaque material (i.e., the first strip 8 is a high radiopacity strip 8), the travel and positioning of the tubular body 2 within the patient may be monitored via X-ray fluoroscopy.

As will become evident from this Detailed Description, the splittable tubular body 2 in its various embodiments provides the following advantages. First, the tubular body 2 is readily splittable between the two types of strips 8, 10 without the presence of a peeling groove, score or skive. Second, the tubular body 2 is less expensive to manufacture than prior art splittable tubular bodies because a peel groove does not need to be formed on the tubular body 2, and the tubular body 2 can be made in a single simple process, such as co-extrusion, co-injection molding, or co-compression molding.

In embodiments of the tubular body 2 that have first strips 8 made of materials that are highly-loaded with radiopaque materials (i.e., tubular bodies 2 with high radiopacity strips 8), such tubular bodies 2 will also have the following advantages. First, because the tubular body 2 is visible in the human body along its entire length via an X-ray fluoroscope, a physician does not need to estimate the position of the extreme end of the distal tip 4 as is required with prior art tubular bodies that have radiopaque rings implanted in their distal ends. Second, because the tubular body 2 is made from compatible polymers or polymeric compounds without the use of pure metals or metallic compounds, the tubular body 2 has better material compatibility and mechanical integrity than prior art tubular bodies. Third, by having a tubular body 2 with both high radiopacity strips 8 and low radiopacity strips 10, the tubular body is highly flexible, yet highly kink resistant. Other advantageous aspects of the tubular body 2 will become apparent throughout this Detailed Description.

Figure 2B:
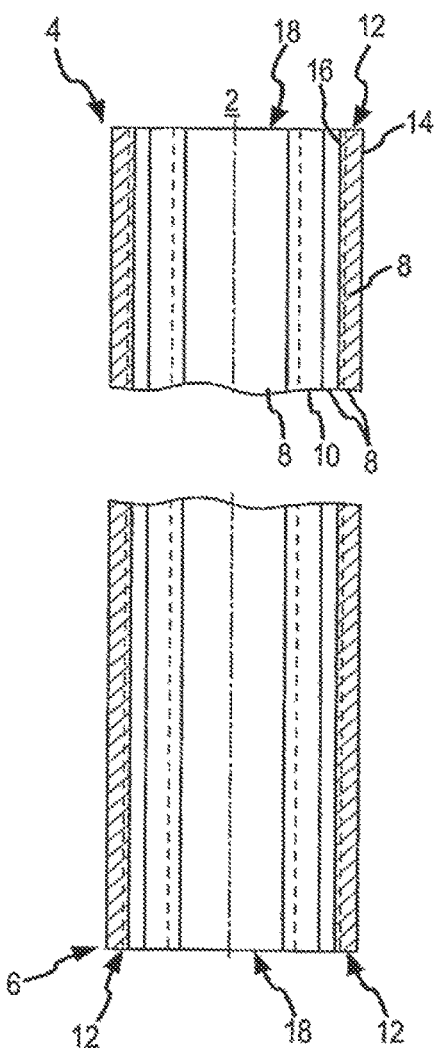
FIG. 2B is a longitudinal cross-sectional view of the first embodiment of the tubular body taken through section line A'-A' in FIG. 2A.

For a better understanding of the first embodiment of the tubular body 2 and its strips 8, 10, reference is now made to FIGS. 2A and 2B. FIG. 2A is a cross-sectional view of the first embodiment of the tubular body 2 taken through section line A-A in FIG. 1. FIG. 2B is a longitudinal cross-sectional view of the first embodiment of the tubular body 2 taken through section line A'-A' in FIG. 2A. As shown in FIGS. 2A and 2B, the first embodiment of the tubular body 2 includes a wall 12 that has an outer circumferential surface 14 and an inner circumferential surface 16. The outer circumferential surface 14 forms the outer surface of the tubular body 2 and the inner circumferential surface 16 defines a lumen 18 through the tubular body 2 that runs the full length of the tubular body 2.

As illustrated in FIG. 2A, each strip 8, 10 forms an integral segment of the wall 12. As shown in FIG. 2A, the tubular body 2, in one embodiment, may have four first strips 8 and four second strips 10 that are formed together (e.g. under a co-extrusion process) to create a wall 12 that is circumferentially continuous and integral along its entire length. In other embodiments, there will be as few as one first strip 8 and one second strip 10. In yet other embodiments, there will be any number of each type of strip 8, 10, including more than four first strips 8 and four second strips 10. Also, in some embodiments, one type of strip 8, 10 will outnumber the other type of strip 8, 10.

In one embodiment with two first strips 8 and two second strips 10, each strip 8, 10 will have a width that comprises approximately 25% of the circumference of the tubular body wall 12. In other embodiments where the strips 8, 10 each account for generally equal percentages of the circumference of the tubular body wall 12, the width of the strips 8, 10, depending on the total number of strips, will range between approximately 2% and approximately 50% of the circumference of the tubular body wall 12.

In one embodiment, one type of strip 8, 10 may constitute a greater percentage of the circumference of the tubular body wall 12. In other words, the first strips 8 may have greater widths than the second strips 10, or vice versa. For example, as illustrated in FIG. 2A, each of the four first strips 8 account for approximately 17% of the circumference of the tubular body wall 12, while each of the second strips 10 each account for approximately 8% of the circumference of the tubular body wall 12. Similarly, in another embodiment with two first strips 8 and two second strips 10, each of the two second strips 10 accounts for approximately 33% of the circumference of the tubular body wall 12, while each of the two first strips 8 accounts for approximately 17% of the circumference of the tubular body wall 12. Again, depending on the number of strips 8, 10, in other embodiments, the width of the strips 8, 10 may range between approximately 2% and approximately 50% of the circumference of the tubular body wall 12. In other embodiments, the width of one or more of the strips 8, 10 will be between approximately 0.1% and approximately 5% to form a micro strip 8, 10.

In one embodiment, one or more of the strips 8, 10 may have a unique percentage of the circumference of the tubular body wall 12. For example, in an embodiment of the tubular body 2 having multiple first strips 8, at least one (if not all) of the first strips 8 has a unique width. Thus, in one embodiment, the widths 8 of the first strips are not all equal. In other embodiments, a similar configuration could exist for at least one (if not all) of the second strips 10 or at least one (if not all) of the strips 8, 10.

In one embodiment, the lumen 18 will have a diameter of between approximately 4 French ("F") and approximately 22 F. In one embodiment, the tubular body 2 will have an outer diameter of between approximately 5 F and approximately 24 F. In one embodiment, the tubular body 2 will have a wall with a thickness of between approximately 0.006" and approximately 0.026".

Figure 4B:
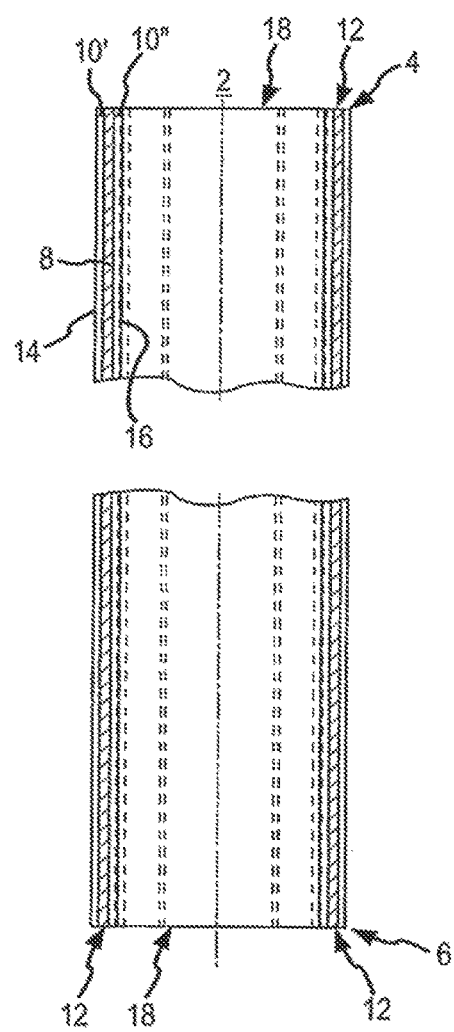
FIG. 4B is a longitudinal cross-sectional view of the second embodiment of the tubular body taken through section line B'-B' in FIG. 4A.

For a discussion of a second embodiment of the invention, reference is now made to FIGS. 3, 4A and 4B. FIG. 3 is an elevational view of a second embodiment of the radiopaque tubular body 2 having a distal end 4 and a proximal end 6 and being formed of at least two integral longitudinal strips 8, 10. These strips 8, 10 can have different radiopacities. FIG. 4A is a latitudinal cross-sectional view of the second embodiment of the tubular body 2 taken through section line B-B in FIG. 3. FIG. 4B is a longitudinal cross-sectional view of the second embodiment of the tubular body 2 taken through section line B'-B' in FIG. 4A.

As can be understood from FIG. 3 and as is more readily seen in FIGS. 4A and 4B, the second embodiment of the tubular body 2 and its strips 8, 10 are configured similarly to those in the first embodiment of the tubular body 2 as depicted in FIGS. 1, 2A and 2B, except the first strips 8 of the second embodiment are subjacent to layers of second strip material 10', 10" that form the outer and inner circumferential surfaces 14, 16 of the tubular body wall 12. In other words, as illustrated in FIGS. 3, 4A and 4B, the first strips 8 of the second embodiment of the tubular body 2 are sandwiched between an outer layer 10' and an inner layer 10" of second strip material 10.

In other variations of the second embodiment, the first strips 8 of the second embodiment of the tubular body 2 are subjacent to a single layer of second strip material 10. For example, in a first variation of the second embodiment of the tubular body 2, as depicted in FIGS. 4C and 4D, which are, respectively, a latitudinal cross-sectional view of the tubular body 2 taken through section line B-B in FIG. 3 and a longitudinal cross-sectional view of the tubular body 2 taken through section line B"-B" in FIG. 4C, the first strips 8 are subjacent to a single layer of second strip material 10, which is an outer layer 10'. Thus, as depicted in FIGS. 4C and 4D, the second strip outer layer 10' forms the outer circumferential surfaces 14 of the tubular body wall 12 and the first strips 8 form segments of the inner circumferential surface 16 of the tubular body wall 12.

Similarly, in a second variation of the second embodiment of the tubular body 2, as depicted in FIGS. 4E and 4F, which are, respectively, a latitudinal cross-sectional view of the tubular body 2 taken through section line B-B in FIG. 3 and a longitudinal cross-sectional view of the tubular body 2 taken through section line B'''-B''' in FIG. 4E, the first strips 8 are subjacent to a single layer of second strip material 10, which is an inner layer 10". Thus, as depicted in FIGS. 4E and 4F, the second strip inner layer 10" forms the inner circumferential surfaces 16 of the tubular body wall 12 and the first strips 8 form segments of the outer circumferential surface 14 of the tubular body wall 12.

For a discussion of a third embodiment of the invention, reference is now made to FIGS. 5, 6A and 6B. FIG. 5 is an elevational view of a third embodiment of the tubular body 2 having a distal end 4 and a proximal end 6 and being formed of at least two integral longitudinal helical strips 8, 10. these strips 8, 10 can have different radiopacities. FIG. 6A is a latitudinal cross-sectional view of the third embodiment of the tubular body 2 taken through section line C-C in FIG. 5. FIG. 6B is a longitudinal cross-sectional view of the third embodiment of the tubular body 2 taken through section line C'-C' in FIG. 6A.

As shown in FIGS. 5, 6A and 6B, in the third embodiment of the tubular body 2, its strips 8, 10 are configured similarly to those in the first embodiment of the tubular body 2 as depicted in FIGS. 1, 2A and 2B, except the strips 8, 10 of the second embodiment extend spirally or helically along the length of the third embodiment of the tubular body 2.

For a discussion of a fourth embodiment of the invention, reference is now made to FIGS. 7, 8A and 8B. FIG. 7 is an elevational view of a fourth embodiment of the tubular body 2 having a distal end 4 and a proximal end 6 and being formed of at least two integral longitudinal helical strips 8, 10. These strips 8, 10 can have different radiopacities. FIG. 8 is a latitudinal cross-sectional view of the fourth embodiment of the tubular body 2 taken through section line D-D in FIG. 7. FIG. 8B is a longitudinal cross-sectional view of the fourth embodiment of the tubular body 2 taken through section line D'-D' in FIG. 8A.

As can be understood from FIG. 7 and as is more readily seen in FIGS. 8A and 8B, the fourth embodiment of the tubular body 2 and its helical strips 8, 10 are configured similarly to those in the third embodiment of the tubular body 2 as depicted in FIGS. 5, 6A and 6B, except the helical first strips 8 of the fourth embodiment are subjacent to layers of second strip material 10', 10" that form the outer and inner circumferential surfaces of the tubular body wall 12. In other words, as illustrated in FIGS. 7, 8A and 8B, the helical first strips 8 of the fourth embodiment of the tubular body 2 are sandwiched between an outer layer 10' and inner layer 10" of second strip material 10.

Figure 8C:
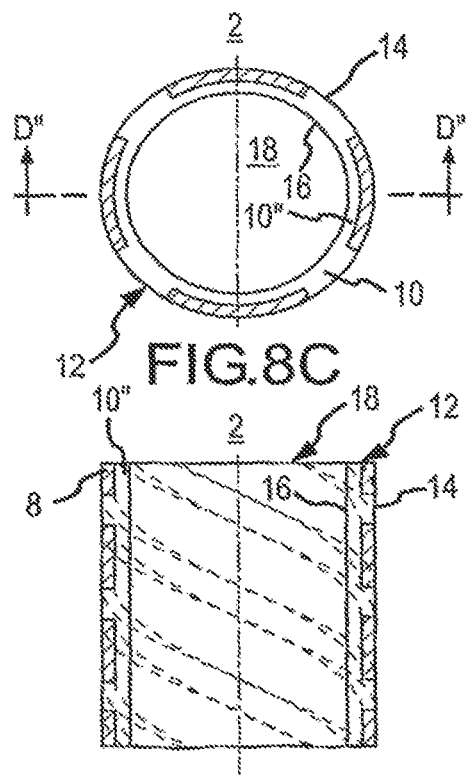
FIG. 8C is a latitudinal cross-sectional view of a first variation of the fourth embodiment of the tubular body taken through section line D-D in FIG. 7.

In other variations of the fourth embodiment, the first strips 8 of the fourth embodiment of the tubular body 2 are subjacent to a single layer of second strip material 10. For example, in a first variation of the fourth embodiment of the tubular body 2, as depicted in FIGS. 8C and 8D, which are, respectively, a latitudinal cross-sectional view of the tubular body 2 taken through section line D-D in FIG. 7 and a longitudinal cross-sectional view of the tubular body 2 taken through section line D"-D" in FIG. 8C, the first strips 8 are subjacent to a single layer of second strip material 10, which is an inner layer 10". Thus, as depicted in FIGS. 8C and 8D, the second strip inner layer 10" forms the inner circumferential surface 16 of the tubular body wall 12 and the first strips 8 form segments of the outer circumferential surface 14 of the tubular body wall 12.

Figure 8E:
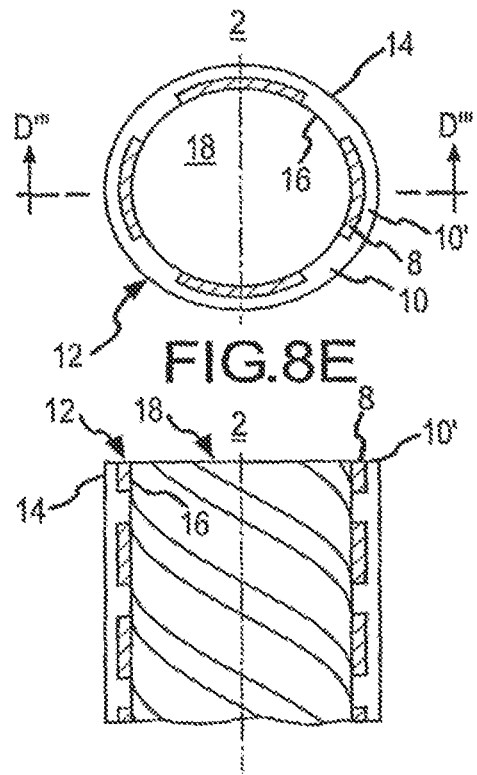
FIG. 8E is a latitudinal cross-sectional view of a second variation of the fourth embodiment of the tubular body taken through section line D-D in FIG. 7.
Figure 8D:
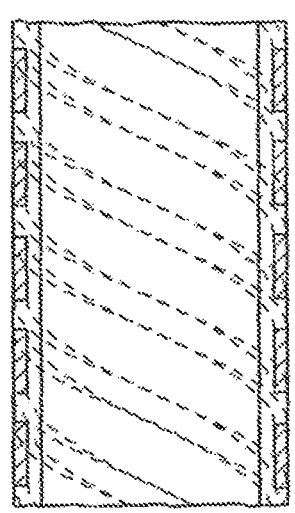
FIG. 8D is a longitudinal cross-sectional view of the first variation of the fourth embodiment of the tubular body taken through section line D"-D" in FIG. 8C.
Figure 8F:
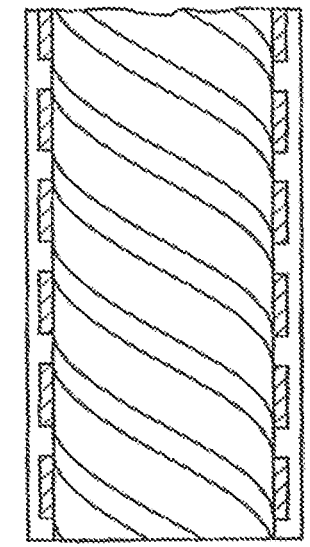
FIG. 8F is a longitudinal cross-sectional view of the second variation of the fourth embodiment of the tubular body taken through section line D'"-D'" in FIG. 8E.

Similarly, in a second variation of the fourth embodiment of the tubular body 2, as depicted in FIGS. 8E and 8F, which are, respectively, a latitudinal cross-sectional view of the tubular body 2 taken through section line D-D in FIG. 7 and a longitudinal cross-sectional view of the tubular body 2 taken through section line D'''-D''' in FIG. 8E, the first strips 8 are subjacent to a single layer of second strip material 10, which is an outer layer 10'. Thus, as depicted in FIGS. 8E and 8F, the second strip outer layer 10' forms the outer circumferential surface 14 of the tubular body wall 12 and the first strips 8 form segments of the inner circumferential surface 16 of the tubular body wall 12.

The first strips 8 and the second strips 10 can be formed from two compatible polymers or polymeric compounds into an integral tubular body 2 via co-extrusion, co-injection molding, or co-compression molding processes. Candidate polymeric materials include thermoplastic and thermosetting polymer systems.

The first strips 8 may be formed of material that is heavily filled with a biocompatible filler of heavy metal or a biocompatible metallic compound that gives rise to high radiopacity under X-ray radiation. The functional width and wall thickness (i.e., percentage of the circumference of the tubular body wall 12) necessary for visibility via X-ray fluoroscopy will vary depending on the degree of radiopacity for a first strip 8 (i.e., high radiopacity strip 8). For example, where a first strip 8 has a high degree of radiopacity (due to the radiopaque nature of the filler of metal or metallic compound impregnated in the polymer and/or due to the percentage of the metal or metallic compound in the polymer), narrower and thinner first strips 8 will suffice. On the other hand, where a first strip 8 has a lower degree of radiopacity, wider and thicker first strips 8 will be required to achieve the necessary visibility via X-ray fluoroscopy.

The first strips 8 (i.e., high radiopacity strips 8), if they are made from elastomeric polymer materials loaded with radiopaque fillers, provide kink resistance for the tubular body 2 in addition to providing the ability to be visualized within a patient's body via X-ray fluoroscopy. In a preferred embodiment, the first strips 8 will be a tungsten-impregnated thermoplastic elastomer, including thermoplastic polyurethane, polyether block amide, and etc. The amount of tungsten used will depend on the degree of radiopacity required and the thermoplastic elastomer. For example, when the strips are formed of PEBAX, the first strip can be loaded with 60-95% by weight tungsten, and preferably 80-85% by weight tungsten.

The second strips 10 (i.e., low radiopacity strips 10) are either not loaded with radiopaque fillers or are lightly loaded. Thus, the second strips 10 have a low radiopacity under X-ray radiation and provide mechanical strength and durability for the tubular body 2.

For melt processing purposes, the selection of the pairs of polymers used for the strips 8, 10 is primarily based on the level of chemical compatibility, balance of mechanical properties, and melt processability between the pairs of polymers. Different grades of polymers having the same constituent chemical species (e.g., various thermoplastic elastomers, including polyether block amides, polyurethanes, olefinics, styrenics, polyesters, polyethers, and etc.) may be used for the pairs. Pairs of thermoplastics and thermoplastic elastomers can also be used (e.g., polyamides with polyether block amides, polyesters with polyether-co-esters). Other polymer pairs are possible with use of polymer compatibilization technologies.

For radiopaque tubular bodies 2, one base polymer from a polymer pair must be filled with heavy metals or metallic compounds using blending and compounding technologies via either melt or solvent processes. The heavy metals and compounds shall be biocompatible (e.g., barium, tungsten, tantalum, platinum, gold, bismuth, zirconium, niobium, titanium, bismuth oxychloride, barium sulfate, bismuth trioxide, iodine, iodide, etc. and their compounds). In one embodiment, the biocompatible radiopaque filler will contain at least one element with an atomic number of from about 22 to about 83.

Filler of a heavy metal or a metallic compound may not be compatible with a selected base polymer, and may cause a drastic decrease in mechanical properties in the heavily loaded polymer compound. To increase the loading level of radiopaque filler and to improve the compatibility of the filler with the base polymer, a compatibilizer or coupling agent can be used for the polymer compound.

As previously noted, the tubular bodies 2 are peelable (i.e., splittable) at one or more border(s) (i.e., interface(s)) between the two types of strips 8, 10. To longitudinally split the tubular body 2, opposite sides of the interior circumferential surface 16 are simply forced apart via a fingernail, tool or other implement. The change in material at the borders between the strips 8, 10 creates a stress concentration point that acts as a built in peel groove along which the tubular body 2 splits when peeled. Thus, no integral peeling groove is needed. However, in some embodiments, as indicated in FIG. 9, an integral peel groove, skive or score 20 is provided to supplement the peelability of the tubular body 2. This can be readily implemented in the embodiments illustrated in FIGS. 1-4. Ideally, this peel groove, skive or score 20 is aligned longitudinally with a boarder between a pair of strips 8, 10. However, the peel groove, skive or score 20 can be located in one of the strips 8, 10 as indicated in FIG. 9. A tubular body 2 can have one or more peel grooves, skives or scores. The peel groove, score or skive 20 can be located in the inner and/or outer circumferential surface of the tubular body 2.

Many of the aforementioned embodiments employ at least one strip 8, 10 formed of a material loaded with a radiopaque material. However, the strips 8, 10 can be formed of polymers that are not loaded with a radiopaque or other materials. For example, the first strips 8 can be formed from a polymer that is dissimilar from the polymer forming the second strips 10. The dissimilarity between the two polymers forming the two strips 8, 10 results in a stress concentration along the interfacial boundary between the two strips 8, 10. The stress concentration serves as a split/peel feature in the tubular body 2 for splitting/peeling the body 2.

The polymers of the strips 8, 10 can be the same polymer, but dissimilar because they have dissimilar molecular orientations. The polymers of the strips 8, 10 can be the same polymer, but dissimilar because they have different toughness, hardness, rigidity, and/or etc. For example, the first or splitting strip 8 can be formed of PEBAX having a durometer value of approximately 70 D, and the second or non-splitting strip 10 is formed of PEBAX having a durometer value of approximately 30-40 D.

In use, a puncture is made with a thin walled needle through the skin and into a blood vessel. A guidewire is then placed through the needle into the blood vessel and the needle is withdrawn. An intravascular introducer is advanced over the guidewire into the lumen of the blood vessel. The tubular body 2 is inserted into the introducer and manipulated so it travels along the blood vessel to the point of treatment (e.g., a chamber in the heart). The travel and positioning of the tubular body 2 within the patient is monitored via X-ray fluoroscopy.

In use, the tubular body 2 is inserted into the body of a patient via a surgical site (e.g., entering the chest cavity below the xiphoid process). A guidewire is used to direct the tubular body 2 to a point of treatment (e.g., the pericardial space of a heart). The travel and positioning of the tubular body 2 within the patient is monitored via X-ray fluoroscopy.

Although the present invention has been described with reference to preferred embodiments, persons skilled in the art will recognize that changes may be made in form and detail without departing from the spirit and scope of the invention.

We claim:

1. A body for a catheter or sheath, the body comprising
a proximal portion,
a distal portion,
at least a first longitudinal strip and a second longitudinal strip,
wherein the at least first and second strips extend generally between the proximal and distal portions and form a wall that is continuous and integral along substantially an entire length and about substantially an entire perimeter of the body while being splittable along an interfacial zone between the first and second strips,
wherein the first longitudinal strip is subjacent to a first layer and a second layer of the second longitudinal strip, wherein the first layer forms an outer circumferential surface of the body and the second layer forms an inner circumferential surface of the body,
wherein the first strip has a radiopacity that is higher than the second strip and
wherein the body has a cylindrical circumference, and wherein the first longitudinal strip comprises between approximately 2% and approximately 50% of the circumference of the cylindrical body.

2. The body of claim 1, wherein the first longitudinal strip comprises between approximately 10% and approximately 25% of the circumference of the tubular body.

3. The body of claim 1, wherein the first and second longitudinal strips are helical along the body.

4. The body of claim 1, wherein the first longitudinal strip is formed from a first polymeric material, wherein the first polymeric material comprises at least one polymer and a biocompatible radiopaque filler of pure metal or metallic compound with at least one element with an atomic number of from about 22 to about 83.

5. The body of claim 1, wherein the first longitudinal strip is formed from a first polymer, wherein the first polymer comprises at least one polymer and tungsten.

6. The body of claim 1, further comprising a third longitudinal strip and a fourth longitudinal strip, wherein the third longitudinal strip comprises a polymeric material, wherein the polymeric material comprises a radiopaque filler, and the third strip and the fourth strip each have a radiopacity, wherein the radiopacity of the third strip is higher than a radiopacity of the fourth strip.

7. The body of claim 6, further comprising a fifth longitudinal strip and a sixth longitudinal strip, wherein the fifth longitudinal strip comprises a polymeric material, wherein the polymeric material comprises a radiopaque filler, and the fifth strip and the sixth strip each have a radiopacity, wherein the radiopacity of the fifth strip is higher than a radiopacity of the sixth strip.

8. The body of claim 1, wherein the first longitudinal strip comprises between approximately 1% and approximately 5% of the circumference of the tubular body.

9. The body of claim 1, wherein the radiopacity of the second strip is zero.

10. A splittable tubular body for a catheter or sheath, the tubular body comprising a peel line formed by a longitudinally extending region of interfacial bonding between first and second longitudinally extending strips of polymeric material, wherein the polymeric material of the first longitudinally extending strip has a molecular orientation that is different from a molecular orientation of the polymeric material of the second longitudinally extending strip, wherein the body is splittable along the peel line without the presence of a peeling groove, score, or skive, and further wherein each longitudinally extending strip forms at least a portion of an outer circumferential surface of the tubular body, and further wherein a region of stress concentration extends along the region of interfacial bonding between the first and second longitudinally extending strips.

11. The splittable tubular body of claim 10, wherein the polymeric material of the first longitudinally extending strip is functionally miscible with the polymeric material of the second longitudinally extending strip.

12. The splittable tubular body of claim 10, wherein the polymeric material of the first longitudinally extending strip is comprised of at least one different polymeric material than the polymeric material of the second longitudinally extending strip.

13. The splittable tubular body of claim 10, wherein the polymeric material of the first longitudinally extending strip is loaded with a greater amount of inorganic filler than the polymeric material of the second longitudinally extending strip.

14. The splittable tubular body of claim 10, wherein the polymeric material of the first longitudinally extending strip is loaded with a greater amount of radiopaque material than the polymeric material of the second longitudinally extending strip.

15. The splittable tubular body of claim 10, wherein the region of stress concentration facilitates the splitting of the tubular body along the peel line.

16. The splittable tubular body of claim 10, wherein the polymeric material of the first longitudinally extending strip is dissimilar from, but chemically compatible with, the polymeric material of the second longitudinally extending strip.

17. The splittable tubular body of claim 10, wherein the polymeric material of the first longitudinally extending strip has a flow-induced axial molecular orientation.

18. The splittable tubular body of claim 10, wherein the polymeric material of the first longitudinally extending strip is not chemically compatible with the polymeric material of the second longitudinally extending strip, and a polymer compatibilizer is introduced into at least one of the polymeric materials to improve melt adhesion between the first and second longitudinally extending strips of polymeric material.

19. The splittable tubular body of claim 10, wherein the polymeric material of the first longitudinally extending strip comprises a first amount of radiopaque filler and the polymeric material of the second longitudinally extending strip comprises a second amount of radiopaque filler, and the first amount is great than the second amount.

* * * * *